United States Patent [19]

Hickle et al.

[11] Patent Number: 5,300,100
[45] Date of Patent: Apr. 5, 1994

[54] BODY WARMER

[75] Inventors: Randall S. Hickle; Patrick J. Griffin, boh of Lubbock, Tex.

[73] Assignee: Advanced Warming Systems, Inc., Lubbock, Tex.

[21] Appl. No.: 570,908

[22] Filed: Aug. 22, 1990

[51] Int. Cl.$^5$ ............................................. A61F 7/00
[52] U.S. Cl. ......................................... 607/107; 5/423
[58] Field of Search ............................... 128/367–389, 128/400, 373, 379, 380; 5/482, 485, 423; 62/259.3; 165/46; 219/212

[56] References Cited

U.S. PATENT DOCUMENTS

| | | | |
|---|---|---|---|
| 1,004,192 | 9/1911 | Phelam | 128/400 |
| 1,356,965 | 10/1920 | Charles | 219/212 |
| 2,110,022 | 3/1938 | Kliesrath | 128/400 |
| 2,601,189 | 6/1952 | Wales | 5/482 |
| 3,757,366 | 9/1973 | Sacher | 128/400 |
| 4,572,188 | 2/1986 | Augustine et al. | 128/380 |
| 4,660,388 | 4/1987 | Greene | 5/485 |
| 4,777,802 | 10/1988 | Feher | 5/482 |
| 4,867,230 | 9/1989 | Voss | 128/402 |

OTHER PUBLICATIONS

We've Removed A Barrier To Better Patient Care . . . Cincinnati Sub–Zero Products, Inc.

Warm Air Hyperthermia System Cincinnati Sub–Zero Products, Inc.

Primary Examiner—Mark S. Graham
Attorney, Agent, or Firm—Tracy Druce; Wendell Coffee

[57] ABSTRACT

Warm air is distributed through a device and diffused along a person's body who is lying under a blanket. Warm air is supplied to the invention from a base unit that has various settings with respect to temperature of air supplied to the invention. The device has three distribution tubes that are long enough to extend from a person's feet to their upper torso while they are lying down. Heating takes place both conductively where the device is in contact with the patient and convectively where the warmed air circulates about the skin. The device is constructed from a light weight tissue paper that is plastic coated on one side and perforated at regular intervals. Heated air is supplied to the invention near the person's feet and is channeled to the several tubes toward the person's upper body. The heated air diffuses through perforations in the tubes as it moves up through the tubes and warms or maintains the body temperature of the patient. Blankets of varying tightnesses of weaves are placed over both the device and the patient thereby holding the desired amount of air near the patient while at the same time insulating against the exterior elements of the environment.

22 Claims, 2 Drawing Sheets

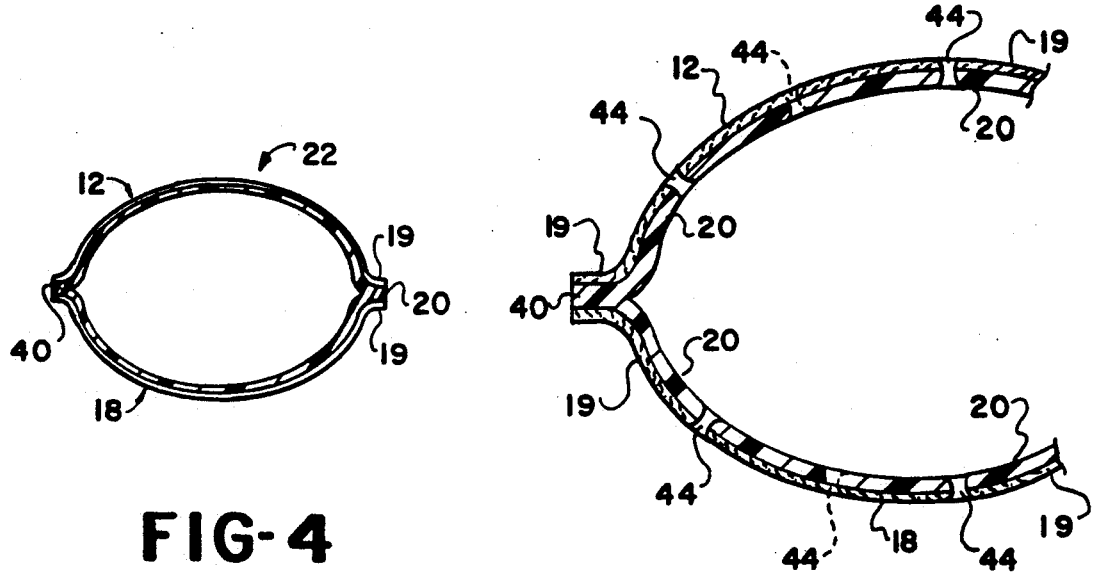
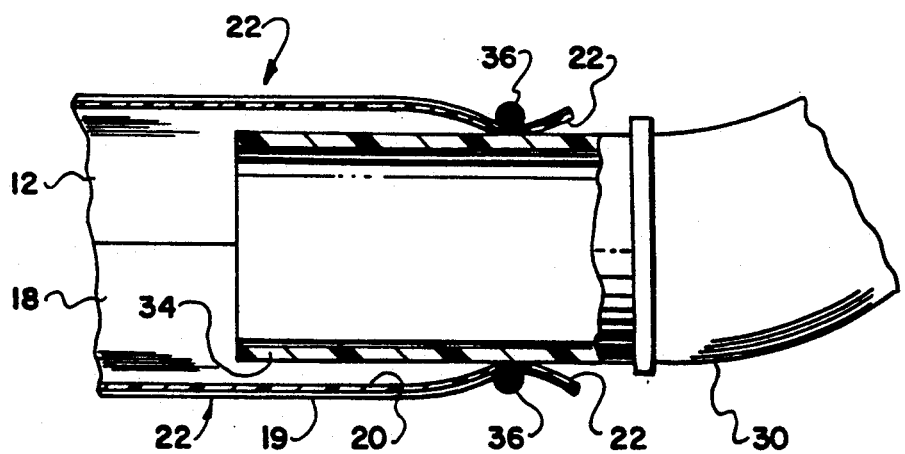

BODY WARMER

BACKGROUND OF THE INVENTION

(1) Field of the Invention

This invention relates to medical devices used to either warm the human body or maintain a normal body temperature. More specifically, it relates to warming devices that use air as the medium in which heat is supplied. Those with ordinary skill in the art are medical personnel who regularly use such equipment.

(2) Description of the Related Art

There are many times when it is desirable to either raise a person's body temperature or maintain it at a normal level. Most of these instances are encountered by medical personnel when dealing with persons who have suffered some sort of physical trauma; these traumas include injuries, surgery, anesthetization and over exposure to extremely cold environmental conditions.

There are times when a person is especially vulnerable to body heat loss when such a loss is most undesirable. This is encountered by medical personnel during and after surgical operations. At these times it is important to maintain the patient's body temperature at a normal level. Maintenance of a body's temperature is often accomplished with warming devices.

A common method used to both raise and maintain a person's body temperature is the use of a blanket. The blanket acts as an insulator by both retaining the patient's body heat and shielding the patient from the external environment. The blanket, however, does not introduce any additional heat. In order to introduce additional heat, electric blankets are sometimes used that have heating elements incorporated into their design.

Another method for raising and maintaining a person's body temperature is to supply warm air to the body surface. One such device is disclosed in U.S. Pat. No. 2,706,988 as a flexible bag that is placed over a portion of the body and then inflated with warm air thereby warming that portion of the body inside the bag. This device is limited to treating localized areas of the body and is not useful in warming the whole person.

A device for both heating and cooling the human body is disclosed in U.S. Pat. No. 2,093,834 in which a blanket type apparatus is used to distribute either cooled or warmed air to a person lying down. The apparatus takes the form of a fabric blanket which has a plurality of layers sewed together to form different enclosures. The enclosure nearest the person diffuses some of the conditioned air to the person while the remainder of the air is forced into a second enclosure forming an inflated insulating air layer about the person. A similar device to that disclosed by Gaugler is seen in U.S. Pat. No. 2,601,189 in which a blanket type bed covering is used to diffuse conditioned air to a person lying on a bed. The blanket consists of an air impervious top layer and an air pervious bottom layer which is next to the person and made from either sponge rubber or a plastic foam. The air diffuses through the bottom layer, thereby cooling or warming the person.

Additional art is disclosed in U.S. Pat. No. 4,572,188 issued to Augustine, et al. The Augustine patent shows a cover that is placed over a person lying down. The cover comprises an array of parallel tubes which run the length of the person's body and are joined together to form a continuous cover over the person. The side of the cover near the patient is perforated, thereby allowing air to escape from the tubes. The side of the cover away from the patient is impervious to air. Conditioned air is supplied to the inflatable tubes which when inflated cause the cover to form a arched enclosure about the patient. The air is channeled through the tubes and distributed about the patient through the perforations on the bottom of the cover. In use, the Augustine device must be fully inflated to form a tentlike structure above the patient's body which terminates at one end above the chest and in front of the face. The inflated cover is both bulky and encumbering to the patient. A confining and restrictive effect is experienced by patients who are recovering from anesthesia since they are often disoriented. The device, being somewhat thick and bulky, must often be moved or removed so that medical personnel may perform routine or emergency procedures involved in patient care.

None of the above described devices provide means for localizing the application of the conditioned air with respect to the patient's body while at the same time having the ability to warm or cool the patient's entire body.

SUMMARY OF THE INVENTION

(1) Progressive Contribution to the Art

A device according to this invention provides a means for distributing conditioned air to a person who is lying down. This device alleviates several of the drawbacks associated with the related art described above. The device has three air distributing tubes that are not permanently joined, but are instead separable. Because the tubes are separable, they can be positioned about the patient's body. This is beneficial when there are either specific areas of the body to be warmed, or there are portions of the body undergoing surgery or that are injured which make it undesirable to have direct air flow on that portion of the patient. Additionally, because the tubes operate independent of each other, each may be folded back on itself at any point to restrict the flow of air beyond that fold. Thisconfiguration is used when a localized warming is required or a limited area of the patient's body is able to tolerate the warmed air.

This invention is operational even when only a low volume of air is being supplied to the patient. This occurs because heating of the patient is accomplished both convectively and conductively. The tubular branches are themselves warm and are designed to rest against the patient thereby conducting heat to the patient where there is skin-to-device contact. Additionally, the diffused warm air heats the patient convectively as the air circulates about the skin surface. This device does not require that the distribution tubes be fully inflated to operate properly; instead, it distributes warmed air to the desired areas even if the tubes are only partially inflated and relatively flat between the patient and the insulating blanket above the invention.

A blanket made of lightweight flexible material is all that is needed to cover the patient with the invention between that blanket and the patient. The type of blanket used is governed by both what is readily available and whether it is desirable to retain the conditioned air under the blanket or to allow the air to diffuse through the blanket causing an exchange of air to take place about the patient. The rate of diffusion is controlled by the tightness of the weave of the blanket. In any event, either type blanket would be readily available in a hospital setting and would most likely be available to paramedics at an accident scene.

In-Use Advance

The structure of the device itself provides several benefits over the related art. The device is formed by placing two panels of the plastic coated paper together so that the plastic sides face one another with the non-abrasive tissue paper to the exterior of the device and next to the patient. This unique design of the invention constitutes a significant "in-use" advance of the art in that it does not impair medical personnel from performing patient care procedures as does prior art. Additionally, the invention provides for both conduction and convection heating of the patient. Furthermore, the invention simplifies the process of patient warming by providing a simplified warm air distributed delivery system whereas prior art provided only for the combination of distributed delivery inseparably bound with an insulating cover.

In-Manufacturing Advance

Thin sheets of pliant and air permeable material are used in the construction of the invention. The embodiment described herein is constructed of a paper-plastic laminate which is both lightweight and inexpensive. The paper-plastic laminate weighs about 40 grams per square yard. While a weight of about 40 grams is preferable, material having weights up to about one-half of a pound per square yard could be used. Because of this simplified design, the invention provides a great "in-manufacturing" advance in the art as the invention can be produced much more efficiently and economically than prior art resulting in a reduction in the cost of medical care.

(2) Objects of this Invention

An object of this invention is to warm a living body.

Another object of the invention is to maintain a body's normal temperature.

Further objects are to achieve the above with devices that are compact, lightweight, simple, safe, versatile, and reliable, yet inexpensive and easy to manufacture and operate.

Other objects are to achieve the above with a method that is rapid, versatile, inexpensive, and does not require highly skilled people to operate and maintain.

The specific nature of the invention, as well as other objects, uses, and advantages thereof, will clearly appear from the following description and from the accompanying drawings, the different views of which are not necessarily scale drawings.

BRIEF DESCRIPTION OF THE DRAWINGS

FIG. 4 is a cross-sectional view along line 4—4 of FIG. 3 showing the branches separated and inflated.

FIG. 5 is an enlarged cross-sectional view along line 5—5 of FIG. 3 of a portion of one of the branches that shows the details of the material used in the construction of the invention.

FIG. 6 is a cross-sectional view along the centerline of the rigid tube showing the trunk of the invention telescoped over the tube with an o-ring surrounding the trunk and tube and seated in a circumferential groove about the tube thereby securing the invention to the warm air supply.

Figure 1:
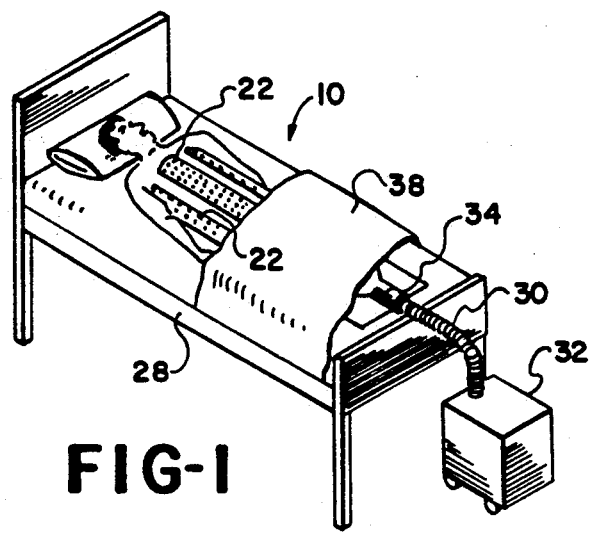
FIG. 1 is an elevation view of a patient lying on a mattress with the invention positioned about that patient and with a blanket over both the patient and the invention.

As an aid to correlating the terms of the claims to the exemplary drawings, the following catalog of elements is provided:

10 body warmer
12 top rectangular panel
4 ends
16 sides
18 bottom rectangular panel
19 tissue paper
20 synthetic plastic coating
22 tubular branch
24 tubular trunk
26 manifold
28 mattress
30 flexible tube
32 base unit
34 rigid tube
36 o-ring
38 light air permeable blanket
40 seams
42 cuts
44 perforations
46 groove
48 closed end

DESCRIPTION OF THE PREFERRED EMBODIMENT(S)

Referring to FIG. 1 of the drawings, a person or patient is shown lying on a mattress 28 with a body warmer 10 positioned about the patient's body. The mattress 28 has sufficient length to accommodate a patient lying down. A tubular branch 22 is positioned between the patient's legs and up onto the patient's torso. Two other tubular branches 22 are positioned alongside the patient and likewise run from the feet to the upper torso of the patient for a total of three tubular branches 22.

Near the feet of the patient and at an end of the mattress 28 is a flexible tube 30 connected to the body warmer 10 by way of a rigid tube 34. The flexible tube 30 serves as a conduit for the warmed air provided by base unit 32 which is a warm air blower that has various settings with respect to temperature of air supplied to the invention. The end of the flexible tube 30 terminates in the rigid tube 34. The rigid tube 34 is properly positioned upon the mattress 28 when its center line is parallel to a lengthwise center line of the mattress 28. In this position, the body warmer 10 is allowed to extend directly from the rigid tube 34 towards the body of the patient. This positioning is required because the body warmer 10 cannot be unintentionally folded or kinked, since folds and kinks will prevent the flow of air beyond the fold.

Light, air-permeable blanket 38 is also seen in FIG. 1 covering both the patient and the body warmer 10. The blanket 38 retains the warmed air that has been diffused by the body warmer 10 near the patient and insulates the patient from the exterior environment.

Figure 2:
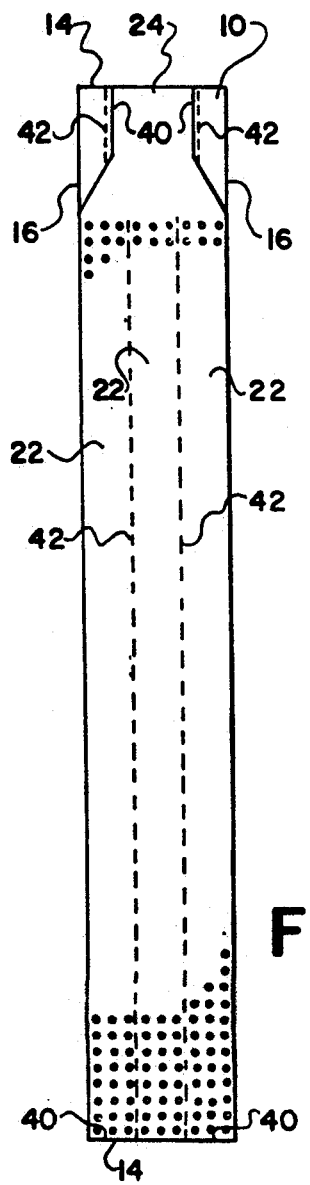
FIG. 2 is a plan view of the invention showing the branches joined together. The diffusing perforations are exaggerated for illustrative purposes.
Figure 3:
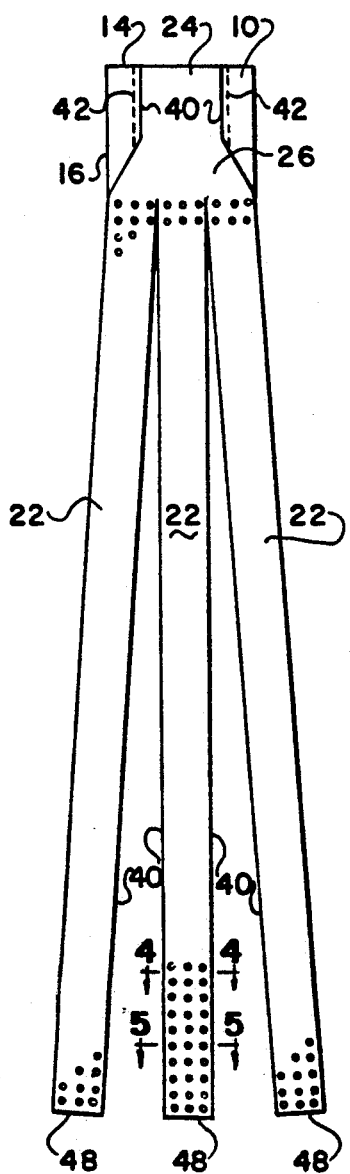
FIG. 3 is a plan view of the invention showing the branches separated.

FIG. 2 shows the body warmer 10 and its different parts. Conditioned air from the flexible tube 30 is introduced to the body warmer 10 through tubular trunk 24 and into manifold 26. From the manifold 26, air is channeled and distributed to the tubular branches 22. The manifold 26 thereby provides fluid communication between the trunk 24 and the tubular branches 22. The air flows from the manifold 26 through the branches 22 toward closed ends 48 of the branches 22 which are away from the manifold 26. The tubular trunk 24 is open at an end of the body warmer 10 which is opposite the closed ends 48 of the branches 22.

As can be seen in FIG. 5, the body warmer 10 is constructed from tissue paper 19 that has a synthetic plastic coating 20 on one side. The plastic reinforced tissue paper weighs about 40 grams per square yard and it has perforations 44 at regular intervals.

The body warmer 10 is formed from a top rectangular panel 12 and a bottom rectangular panel 18 which are placed one on top of the other so that the plastic coated side of each panel 12 and 18 is face to face and contacting each other. The rectangular panels 12 and 18 both have ends 14 and sides 16 which have dimensions equal to those of the body warmer 10. The lengths of ends 14 and sides 16 are equal to the width and length of the panels 12 and 18, respectively. The width of the rectangular panels 12 and 18 and the body warmer 10 is about nine inches while the length is about 65 inches which is about 0.9 times the length of the mattress 28. Additionally, the length of each of the panels 12 and 18 is about seven times the width of the panels 12 and 18. A length of 65 inches is preferred. Lengths less than 55 inches make it difficult to warm a person of average height.

The body warmer 10 is sectioned into the several parts seen in FIG. 2 by way of seams 40. The seams 40 can be created by adhering the panels 12 and 18 together in different ways: the seams 40 can be established by joining the panels 12 and 18 with glue or by fusing the plastic together in a heat and pressure process applied along the lines where the seams 40 are desired. The seams 40 define the manifold 26 as well as the branches 22 and the trunk 24. There are cuts along the outside of the seams 40 that define the trunk 24 thereby separating excess panel material from the trunk 24.

The trunk 24 has a width of about one-half the width of the body warmer lo. The manifold 26 expands from a narrow width equal to that of the trunk 24 to which it connects at a narrow end to a width equal to that of the body warmer 10 where the manifold 26 connects to the branches 22. Connection between the branches 22 and the manifold 26 causes adjacent branches 22 to remain proximate to each other at the ends of said branches 22 joined to the manifold 26. The branches 22 each have a width of about one-third the width of the body warmer 10. The length of the branches 22 is more than two-thirds the length of the panels 12 and 18.

The branches 22 do not share a common seam 40 between them; instead, there are different seams 40 for the edge of each branch 22. By having two adjacent seams 40, the material between the two adjacent seams 40 of two adjoined branches 22 may be split along cuts 42, also referred to as tear perforations, thereby separating the two adjoining branches 22. The cut 42 serves as a separation separating each tubular branch 22 from adjacent tubular branches 22. The cut 42 or separation between the tubular branches 22 extends from the closed ends 48 of said branches 22 toward the manifold 26 so that said branches 22 may be oriented farther apart from each other at the closed ends 48 than at the ends joining the manifold.

The preferred embodiment shown in the drawings discloses a body warmer 10 with three branches 22; the invention may have a plurality of branches, but should have at least two branches for adequate air distribution.

An alternative embodiment would have one seam 40 between adjoined branches with that seam 40 having a fused width adequate to allow a cut down its center while maintaining a tight seal at the edge of each branch 22 on either side of that seam 40. There are seams 40 at the closed ends 48 of the branches 22 away from the manifold 26 thereby forming the branches 22 into tubes; each branch 22 closed at end 48 and open at the end that is in communication with the manifold 26.

The connection of the body warmer 10 to the air supplying flexible tube 30 is shown in FIG. 6. At the end of flexible tube 30 is the rigid tube 34 over which the tubular trunk 24 is telescoped. An effective seal between the trunk 24 and the rigid tube 34 is accomplished by rolling o-ring 36 down about the exterior of the trunk 24, thereby surrounding the trunk 24 and the tube 34. The best mode contemplated includes a circumferential indentation or groove about the rigid tube 34, but inclusion of the groove 46 has proven cost prohibitive in actual production.

The embodiment shown and described above is only exemplary. I do not claim to have invented all the parts, elements or steps described. Various modifications can be made in the construction, material, arrangement, and operation, and still be within the scope of my invention.

The restrictive description and drawings of the specific examples above do not point out what an infringement of this patent would be, but are to enable one skilled in the art to make and use the invention. The limits of the invention and the bounds of the patent protection are measured by and defined in the following claims.

We claim:

1. A body warmer comprising:
    a. a top panel having
        i. ends, and the distance across the ends being the width of the panel, and
        ii. sides, and the distance along the sides being the length of the panel,
    b. a bottom panel having the same size and shape as the top panel,
    c. said panels each being a thin sheet of lightweight, permeable, and pliant material,
    d. said top panel face-to-face with and contacting the bottom panel,
    e. said panels joined together to form a plurality of tubular branches connected to a tubular trunk by a manifold,
    ee. the manifold providing fluid communication between the trunk and the tubular branches.
    f. all the branches closed at one end of the panels,
    g. said trunk being open at the end of the panels opposite the end where the trunks are closed,
    hh. each tubular branch separated by a separation from adjacent tubular branches.
    jj. adjacent branches remain proximate to each other at the ends of said branches joined to the manifold, and
    kk. the separation between the tubular branches extends from the closed ends of said branches toward the manifold so that said branches may be oriented farther apart from each other at the closed ends than at the ends joining the manifold.
2. The body warmer as defined in claim 1 wherein there are least three branches.
3. The body warmer as defined in claim 1 with the addition of means for blowing warm air into the body warmer through the trunk thereof.
4. The body warmer as defined in claim 3 wherein the length of the panels is at least 55 inches.
5. The body warmer as defined in claim 3 wherein said panels together weight less than one-half of a pound.
6. The body warmer as defined in claim 1 further comprising:
  h. the branches adapted to be positioned about a patient and rest against said patient, and
  j. a light air permeable blanket covering the body warmer and patient.
7. A body warmer comprising:
  a. a top panel having
    i. ends, and the distance across the ends being the width of the panel, and
    ii. sides, and the distance along the sides being the length of the panel,
  b. a bottom panel having the same size and shape as the top panel,
  c. said panels each being tissue paper with a synthetic plastic coating on one side and perforated,
  d. said top panel over the bottom panel with the plastic coating side of each panel face-to-face with and contacting the plastic coating side of the other panel,
  e. said panels adhered together to form three tubular branches joined to a tubular trunk by manifold,
  ee. the manifold providing fluid communication between the trunk and the tubular branches,
  f. each branch having a width equal to about ⅓ the width of the panels and length of more than two thirds the length of the panels,
  g. all the branches closed at one end of the panels,
  jj. each tubular branch separated by a separation from adjacent tubular branches,
  kk. adjacent branches remain proximate to each other at the ends of said branches joined to the manifold,
  ll. the separation between the tubular branches extends from the closed ends of said branches toward the manifold so that said branches may be oriented farther apart from each other at the closed ends than at the ends joining the manifold,
  j. the trunk having a width of about one half the width of the panels, and
  k. said trunk being open at the end of the panels opposite the end where the panels are closed.
8. The body warmer as defined in claim 7 with the addition of
  l. a mattress having a length for a hospital patient,
  m. said body warmer above said mattress, and
  n. the length of the panels being about 0.9 times the length of the mattress.
9. The body warmer as defined in claim 7 further comprising:
  1. the length of the panel being about seven times the width of the panel.
10. The body warmer as defined in claim 7 further comprising:
  1. said plastic coated tissue paper panels cut outside the trunk on each side of the trunk.
11. The body warmer as defined in claim 7 with the addition of means for blowing warm air into the body warmer through the trunk thereof.
12. The body warmer as defined in claim 11 with the addition of said means for supplying warm air has
  l. a flexible tube extending from
  m. a base unit,
  n. said flexible tube terminating with rigid tube having a circumference less than twice the width of the trunk,
  o. said trunk telescoped over said rigid tube, and
  p. a band surrounding the trunk and the rigid tube thereby holding the trunk onto the rigid tube.
13. The body warmer as defined in claim 7 wherein the plastic reinforced tissue paper weighs about 40 grams per square yard.
14. The body warmer as defined in claim 13 with the addition of
  l. a mattress having a length for a hospital patient,
  m. said body warmer above said mattress, and
  n. the length of the panels being about 0.9 times the length of the mattress.
15. The body warmer as defined in claim 14 further comprising:
  o. the length of the panel being about seven times the width of the panel.
16. The body warmer as defined in claim 15 with the addition of means for blowing warm air into the body warmer through the trunk thereof.
17. The body warmer as defined in claim 18 with the addition of said means for supplying warm air has
  p. a flexible tube extending from
  q. a base unit,
  r. said flexible tube terminating with rigid tube having a circumference less than twice the width of the trunk,
  s. said trunk telescoped over said rigid tube, and
  t. a band surrounding the trunk and the rigid tube thereby holding the trunk onto the rigid tube.
18. The body warmer as defined in claim 17 further comprising:
  u. the plastic coated tissue paper panels cut outside the trunk on each side of the trunk.
19. The body warmer as defined in claim 7 further comprising:
  l. the branches adapted to be positioned about a patient and rest against said patient, and
  m. a light air permeable blanket covering the body warmer and patient.
20. The body warmer as defined in claim 18 further comprising:
  v. the branches adapted to be positioned about a patient and rest against said patient, and
  w. a light air permeable blanket covering the body warmer and patient.
21. A body warmer on a mattress beneath a light air permeable blanket comprising in combination with the above:
  a. a top and bottom perforated panel of tissue paper,
  b. each panel coated with a synthetic plastic,
  c. said panels adhered together to form three tubular branches joined to a tubular trunk by manifold,
  d. each tubular branch separated by a separation from adjacent tubular branches,
  e. adjacent branches remain proximate to each other at the ends of said branches joined to the manifold,
  f. the separation between the tubular branches extends from the closed ends of said branches toward the manifold so that said branches may be oriented farther apart from each other at the closed ends than at the ends joining the manifold,
g. the manifold providing fluid communication between the trunk and the tubular branches, and
h. a flexible tube connecting
j. a warm air blower to the trunk.

22. The body warmer as defined in claim 21 further comprising:
k. the branches adapted to be positioned about a patient and rest against said patient, and
l. a light air permeable blanket covering the body warmer and patient.

* * * * *